(12) United States Patent
Siccardi et al.

(10) Patent No.: US 10,905,444 B2
(45) Date of Patent: Feb. 2, 2021

(54) PATIENT-SPECIFIC NAVIGATIONAL GUIDE

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Alberto Lipari, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 52 days.

(21) Appl. No.: 16/333,057

(22) PCT Filed: Sep. 15, 2017

(86) PCT No.: PCT/IB2017/055588
§ 371 (c)(1),
(2) Date: Mar. 13, 2019

(87) PCT Pub. No.: WO2018/055494
PCT Pub. Date: Mar. 29, 2018

(65) Prior Publication Data
US 2019/0201013 A1 Jul. 4, 2019

(30) Foreign Application Priority Data
Sep. 23, 2016 (IT) ........................ 102016000095913

(51) Int. Cl.
*A61B 17/17* (2006.01)
*A61B 17/88* (2006.01)
(Continued)

(52) U.S. Cl.
CPC ...... *A61B 17/1757* (2013.01); *A61B 17/8897* (2013.01); *A61B 2017/568* (2013.01); *A61B 2034/108* (2016.02)

(58) Field of Classification Search
CPC ...................... A61B 17/1757; A61B 2017/568
See application file for complete search history.

(56) References Cited

U.S. PATENT DOCUMENTS 8,758,357 B2   6/2014  Frey
8,870,889 B2 * 10/2014  Frey ...................... B33Y 80/00
                                                606/96
(Continued)

FOREIGN PATENT DOCUMENTS

DE         4219939 A1   12/1993
EP         2502582 A1    9/2012
(Continued)

OTHER PUBLICATIONS

International Search Report and Written Opinion of the EP International Searching Authority. Application No. PCT/IB2017/055588. dated Nov. 22, 2017. 13 pages.
(Continued)

*Primary Examiner* — Ellen C Hammond
(74) *Attorney, Agent, or Firm* — Meunier Carlin & Curfman LLC

(57) ABSTRACT

A patient-specific navigational guide for use in spinal surgery, comprising two tubular guiding members integral with a supporting frame and extending from a proximal opening to a distal opening for guiding a surgical operation on a patient's vertebra. The contact members are designed to mate with a corresponding plurality of contact areas on the patient's vertebra in order to define a unique coupling configuration of the patient-specific navigational guide on the patient's vertebra. Said contact members comprise at least one pair of a first main contact member, designed to abut, at least partially, on the upper articular process, or facet, of the patient's vertebra, and a pair of second main contact members, designed to abut on a contact area corresponding to the lamina of the patient's vertebra. Said tubular
(Continued)

guiding members each have a slot extending from the proximal opening to the distal opening.

13 Claims, 5 Drawing Sheets

(51) Int. Cl.
    *A61B 17/56*     (2006.01)
    *A61B 34/10*     (2016.01)

(56) References Cited

U.S. PATENT DOCUMENTS

| | | |
|---|---|---|
| 9,198,678 B2 | 12/2015 | Frey et al. |
| 9,642,633 B2 | 5/2017 | Frey et al. |
| 9,987,024 B2 | 6/2018 | Frey et al. |
| 2002/0123668 A1 | 9/2002 | Ritland |
| 2007/0066977 A1 | 3/2007 | Assell et al. |
| 2008/0114370 A1 | 5/2008 | Schoenefeld |
| 2013/0053854 A1 | 2/2013 | Schoenefeld et al. |

FOREIGN PATENT DOCUMENTS

| | | | |
|---|---|---|---|
| EP | 2749235 A1 | 7/2014 | |
| TW | 200908927 A | 3/2009 | |
| WO | 9600049 A1 | 1/1996 | |
| WO | 2013/158521 A1 | 10/2013 | |
| WO | 2014/070889 A1 | 5/2014 | |
| WO | WO-2014090908 A1 * | 6/2014 | ......... A61B 17/1757 |
| WO | 2014/197844 A1 | 12/2014 | |
| WO | 2016/075581 A1 | 5/2016 | |
| WO | 2016075660 A1 | 5/2016 | |

OTHER PUBLICATIONS

English Translation of Notice of Reasons of Refusal in JP 2019-536348, dated Feb. 27, 2020, 14 pages.

Radermacher, Klaus, Computer Assisted Orthopaedic Surgery with Individual Templates, Helmholtz-Institute for Biomedical Engineering, 2 pages, 1997.

Berry et al., Personalised image-based templates for intra-operative guidance, Proceedings of the Institution of Mechanical Engineers, Part H: Journal of Engineering in Medicine, vol. 219, pp. 111-118, 2004.

Lu et al., A Novel Patient-Specific Navigational Template for Cervical Pedicle Screw Placement. SPINE, vol. 34, No. 26, pp. E959-E964, 2009.

Popescu et al., Design and Rapid Manufacturing of Patient-Specific Spinal Surgical Guides: A Survey, Proceedings in Manufacturing Systems, vol. 7, Issue 2, pp. 115-120, 2012.

Lu et al., A novel computer-assisted drill guide template for placement of C2 laminar screws, Eur Spine J, vol. 18, pp. 1379-1385, 2009.

Lu et al., Rapid prototyping drill guide template for lumbar pedicle screw placement, Chinese Journal of Traumatology, vol. 12(3), pp. 171-177, 2009.

Ryken et al., Image-based drill templates for cervical pedicle screw placement, J Neurosurg Spine vol. 10, pp. 21-26, 2009.

Brussel et al., Medical Image-Based Design of an Individualized Surgical Guide for Pedicle Screw Insertion, 18th Annual International Conference of the IEEE Engineering in Medicine and Biology Society, Amsterdam, pp. 225-226, 1996.

\* cited by examiner

PATIENT-SPECIFIC NAVIGATIONAL GUIDE

TECHNICAL FIELD

The present invention relates to the technical field of orthopaedic surgery. More specifically, the invention relates to a patient-specific navigational guide to be employed in spinal surgery.

Patient-specific guides are disposable templates, which are individually designed to match the bone anatomy derived from computed tomography images of a given patient. Surgical operations like drills and cuts can be pre-operatively planned by computer-aided technologies, and the resulting patient-specific guides will later allow the surgeon to accurately replicate the planned operations on the patient's body.

Patient-specific guides have been employed in several fields of orthopaedic surgery, including spinal surgery.

In this field, patient-specific guides are mainly employed to help the surgeon during pedicle screw insertion, so that the screw can be inserted according to a pre-planned optimal axis thereof.

However, patient-specific guides may be used in spinal surgery for other purposes; for instance as cutting guides during PSO (pedicle substraction osteotomies), laminotomy or facectomies.

STATE OF THE ART

Examples of patient-specific guides are known, for example, from patents EP2749235, EP2502582, WO2013/158521, WO2014/197844, or still WO2014/070889, WO2016/075581.

As is known in the state of the art, navigational guides comprise two or more tubular guiding members integral with a supporting frame.

The two tubular guiding members define the insertion axes for two pedicle screws, which can be inserted in the vertebra of the patient according to a pre-operatively planned angle. The insertion axes correspond to the longitudinal axes of the tubular guiding members. Therefore, the tubular guiding members have a through axial cavity through which a surgical tool can be inserted, for example in order to prepare the pedicle to receive the pedicle screw. A typical example of a pedicle screw used in this kind of surgery is a cannulated pedicle screw, having a through axial cavity that extends over the entire length of the pedicle screw.

The inner diameter of the tubular guiding members is such as to allow the insertion of a guide wire, for example a Kirchner wire. The Kirchner wire is thus implanted, by means of known guides, in the patient's vertebra. A cannulated pedicle screw is then fitted on the Kirchner wire and slid along it until the end of the threaded shank of said cannulated pedicle screw contacts the vertebra. At this point, the surgeon proceeds, by means of special instruments, to insert said cannulated pedicle screw inside the vertebra.

To enable the cannulated pedicle screw to contact the bone surface, the tubular guiding members must have a diameter large enough to accommodate therein the cannulated pedicle screw, being obviously oversized with respect to the diameter of a guide wire.

This over-sizing of the tubular guiding members does not allow precise positioning of the Kirchner guide wire with respect to the vertebra, nullifying the pre-operative planning.

In order to overcome this drawback, sleeves were provided, which were to be inserted within the tubular guiding members. Said sleeves have a through axial cavity, which is coaxial with the longitudinal axis of the tubular guiding members, sized to fit therein and adapted to accommodate the Kirchner guide wire. In this way, the positioning of the Kirchner guide wire is sufficiently accurate.

However, it will be necessary for the surgeon to carry out the indispensable actions of coupling the sleeves within the tubular guiding members, placing the navigational guide in situ, inserting the Kirchner guide wires, and extracting the navigational guide.

In addition to the increased number of steps required of the surgeon to be carried out in the presence of body fluids, which make them difficult to perform, however, the drawback, common to all known navigational guides, of how to remove said navigational guide once the Kirchner guide wires have been positioned, avoiding to act on said guide wires, remains unsolved.

In fact, a common feature of the tubular guiding members of known navigational guides is that of having a longitudinal axis inclined relative to the sagittal plane, specularly to each other. Said inclined longitudinal axis determines the insertion path for the Kirchner guide wire that will be parallel thereto once implanted. This inclination of the longitudinal axis makes the removal of the navigational guide, once the Kirchner guide wire has been implanted, until the Kirchner guide wire comes out of its seat, very complicated and awkward.

However, although inconvenient for the surgeon, such an inclination of the longitudinal axes of the guiding members is important for proper positioning of the K-wires/pedicle screw, so as not to cause damage to the bone structures of the patient. It is therefore clear that the navigational guide must have a rigid structure, which does not allow movements of the tubular guiding members. In the light of the above, it is clearly difficult for the surgeon to remove the navigational guide when the K-wire is implanted in the patient's vertebra, a difficulty increased by the intrinsic rigidity of the structure of the navigational guide.

To solve this problem, in the state of the art, navigational guide for stiffening structures, such as non-straight bridges, was provided. Said non-straight bridges, while performing the stiffening action, considerably increase the dimensions of the navigational guide in the cranial-caudal direction, therefore requiring space to be inserted.

This resulted in increased size of the wound inflicted on the patient in order to be able to properly access the operative site, and also proved difficult to implement when the operation involved small vertebrae, such as for example the cervical vertebrae.

OBJECT OF THE INVENTION

In view of the foregoing, the technical problem underlying the present invention is to provide a patient-specific surgical guide of the type used in spinal surgery, which allows proper implantation of a guide wire and consequent removal of the patient-specific surgical guide, preventing interference phenomena between said surgical guide and the guide wire. Specifically, the technical problem that the present invention aims to solve is that of providing a patient-specific surgical guide of the type used in spinal surgery, which is quick and easy to position and remove, less invasive for the patient, and involves just a few steps for the surgeon to perform for its insertion, thus limiting the margin of error.

The aforementioned technical problem is solved by means of a patient-specific navigational guide for use in spinal surgery, according to claim 1. The invention eliminates the risk of interference between the guide wire and the patient-specific navigational guide by means of lateral openings through which the implanted guide wire can be extracted. This prevents the surgeon from having to act on the implanted guide wires in order to extract the patient-specific navigational guide from the operative site. In this way, the guide wires are not handled after their implantation, avoiding escape of the same from the patient's bone, which would require repositioning. Thanks to this, the surgeon is relieved of a task, the surgery has fewer risks, surgery time is reduced as well as the chances of incorrect positioning of the prosthetic implant.

The presence of lateral openings in the tubular guiding members allows correct positioning of the guide wires, ensuring quick and easy removal of the patient-specific navigational guide. The structure of the guide, by having at least 4 resting points, ensures correct and precise positioning on the patient's vertebra.

The guide according to the present invention is suitable for the cervical, thoracic and lumbar spine, and the sacrum.

Further features and advantages of the patient-specific navigational guide according to the invention will become more apparent from the description, provided hereinbelow, of a number of embodiments described by way of non-limiting example with reference to the accompanying drawings.

DETAILED DESCRIPTION OF PREFERRED EMBODIMENTS OF THE INVENTION

Figure 1:
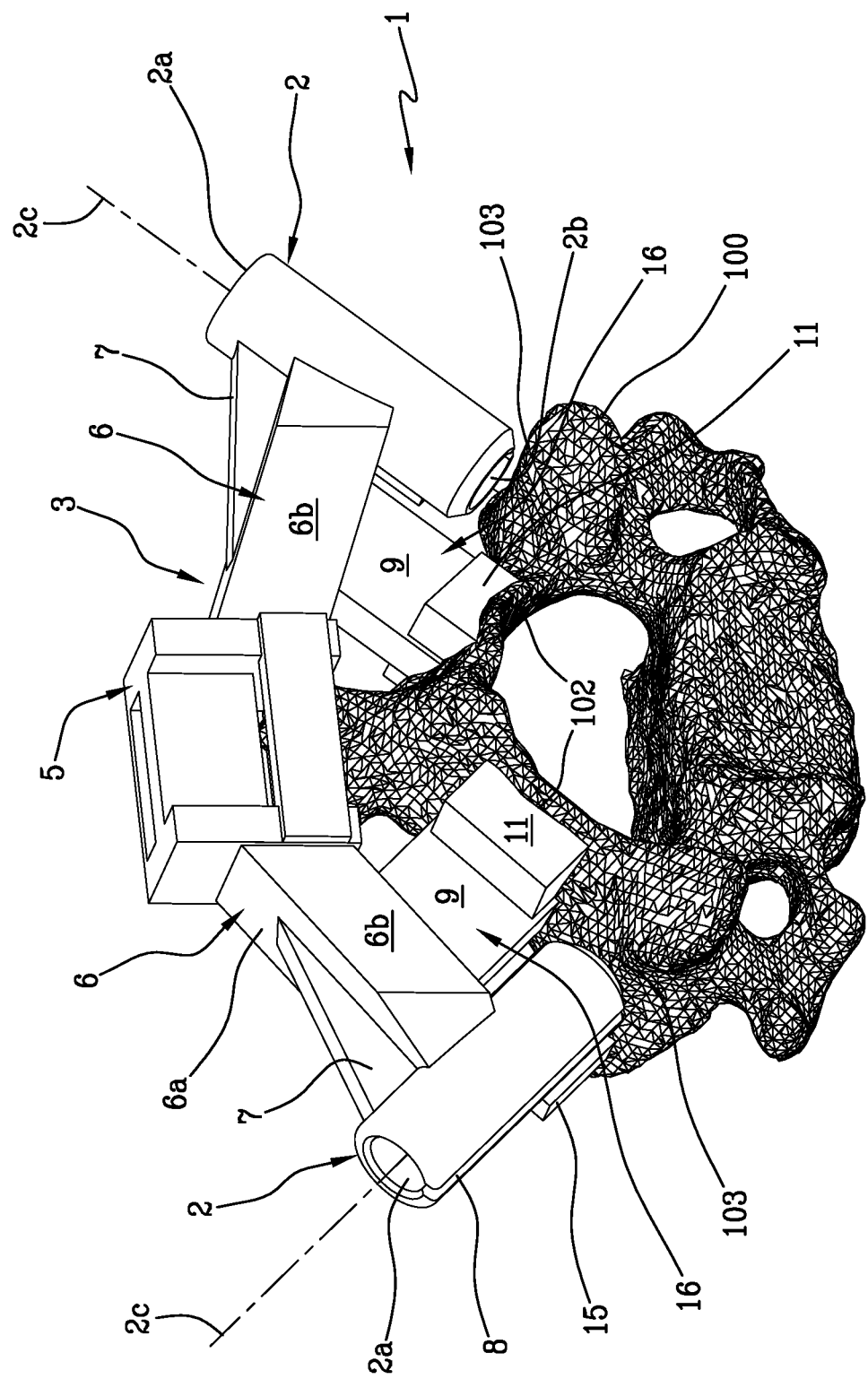
FIG. 1 is a front perspective view of the patient-specific navigational guide.

Referring to FIGS. 1 to 4, an exemplary embodiment of a patient-specific navigational guide 1 for spinal surgery is shown, which is specifically designed for surgery on a vertebra 100.

As can be readily recognized in these figures, the navigational guide 1 comprises two tubular guiding members 2.

The two tubular guiding members are integral with a supporting frame 3. The two tubular guiding members 2 define the insertion axes for guide wires or for two pedicle screws, which can be inserted in the (preferably cervical) vertebra according to a pre-operatively planned angle. The insertion axes correspond to the longitudinal axes 2c of the tubular guiding members 2. Therefore, the tubular guiding members 2 have a proximal opening 2a, where a surgical instrument can be inserted, and a distal opening 2b in the vicinity of the patient's vertebra. The terms "proximal" and "distal" are used with reference to the surgeon.

The two tubular guides 2 have respective longitudinal axes 2c, mutually inclined and converging on a distal point.

The inner diameter of the tubular guiding members 2 is such as to allow the insertion of a Kirchner wire. The Kirchner wire (K-wire hereinbelow) is implanted into the bone and, when the guide 1 is removed, is used to guide a polyaxial screw which runs along the K-wire in order to touch the bone and be implanted therein. The inner diameter of the tubular guiding members 2 can be large enough to allow the passage of a polyaxial screw or a bone resection instrument, such as a burr. The inner diameter of the tubular guiding members 2 can be selected from 3-18 mm, 3-12 mm, 3-9 mm, 3-6 mm.

The distal opening 2b may comprise an opening so that the surgeon can check the entry point of the pedicle screw or Kirchner wire inserted through the tubular guiding members 2.

Figure 2:
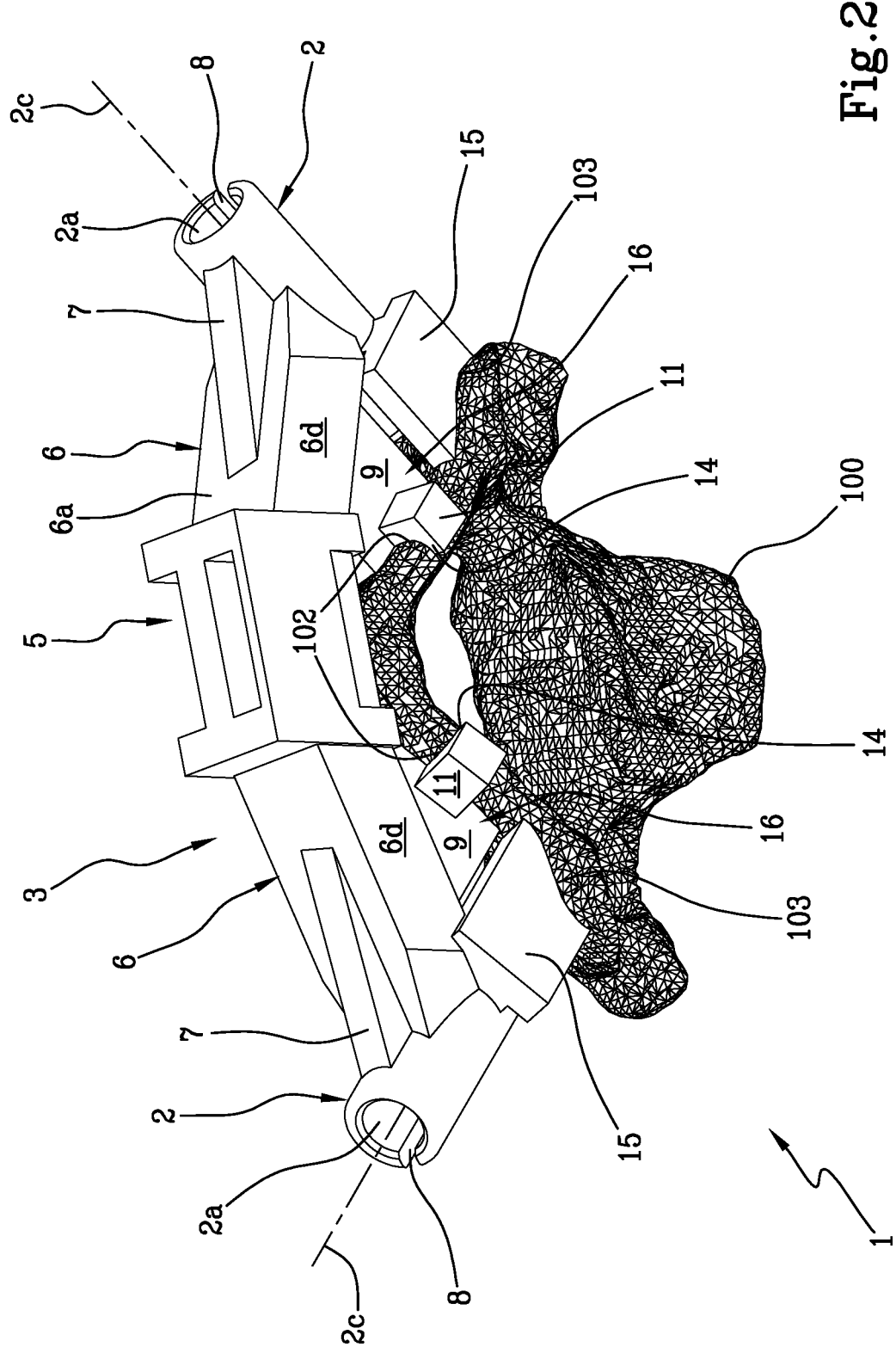
FIG. 2 is a rear perspective view of the patient-specific navigational guide.
Figure 3:
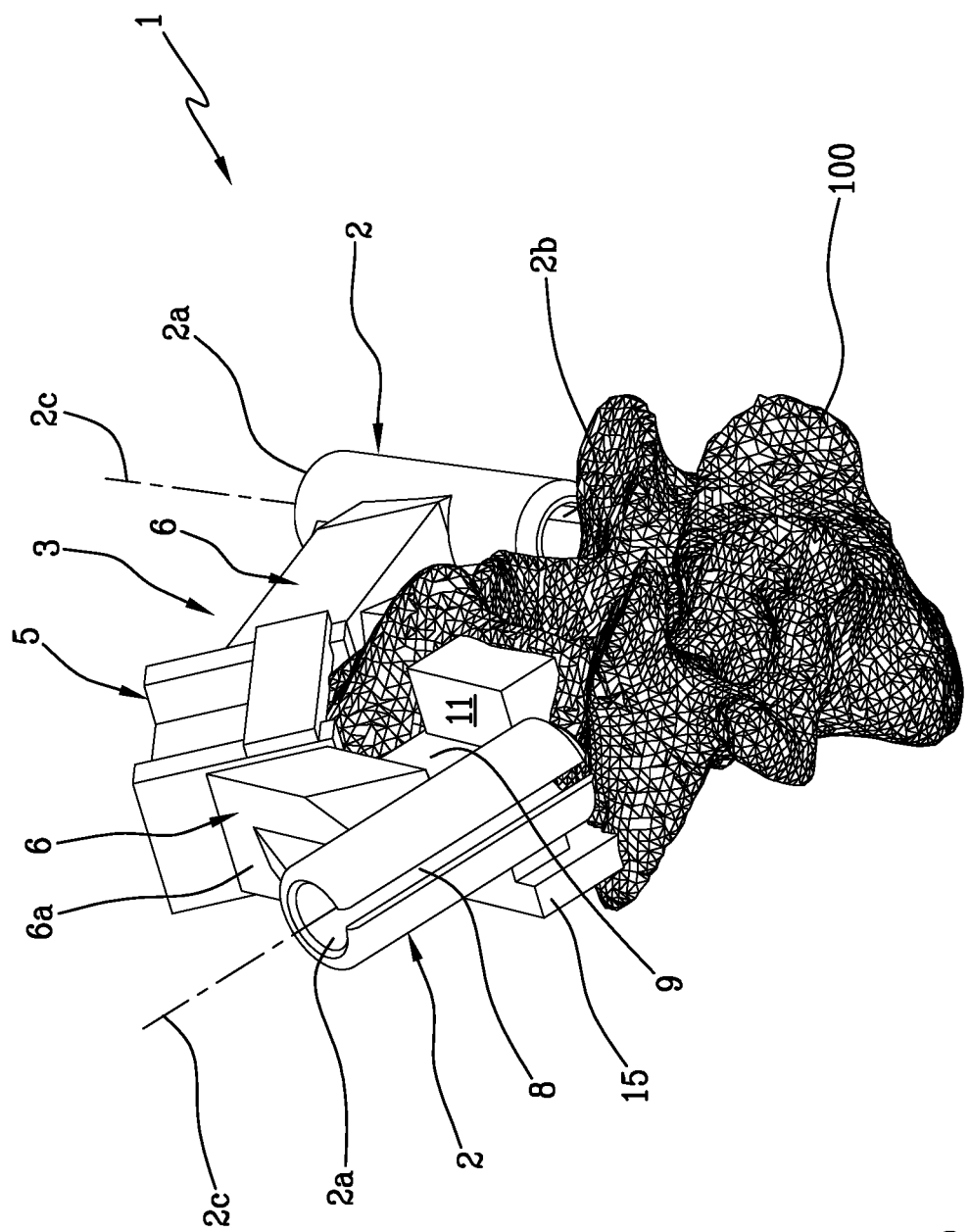
FIG. 3 is a side perspective view of the patient-specific navigational guide.
Figure 4:
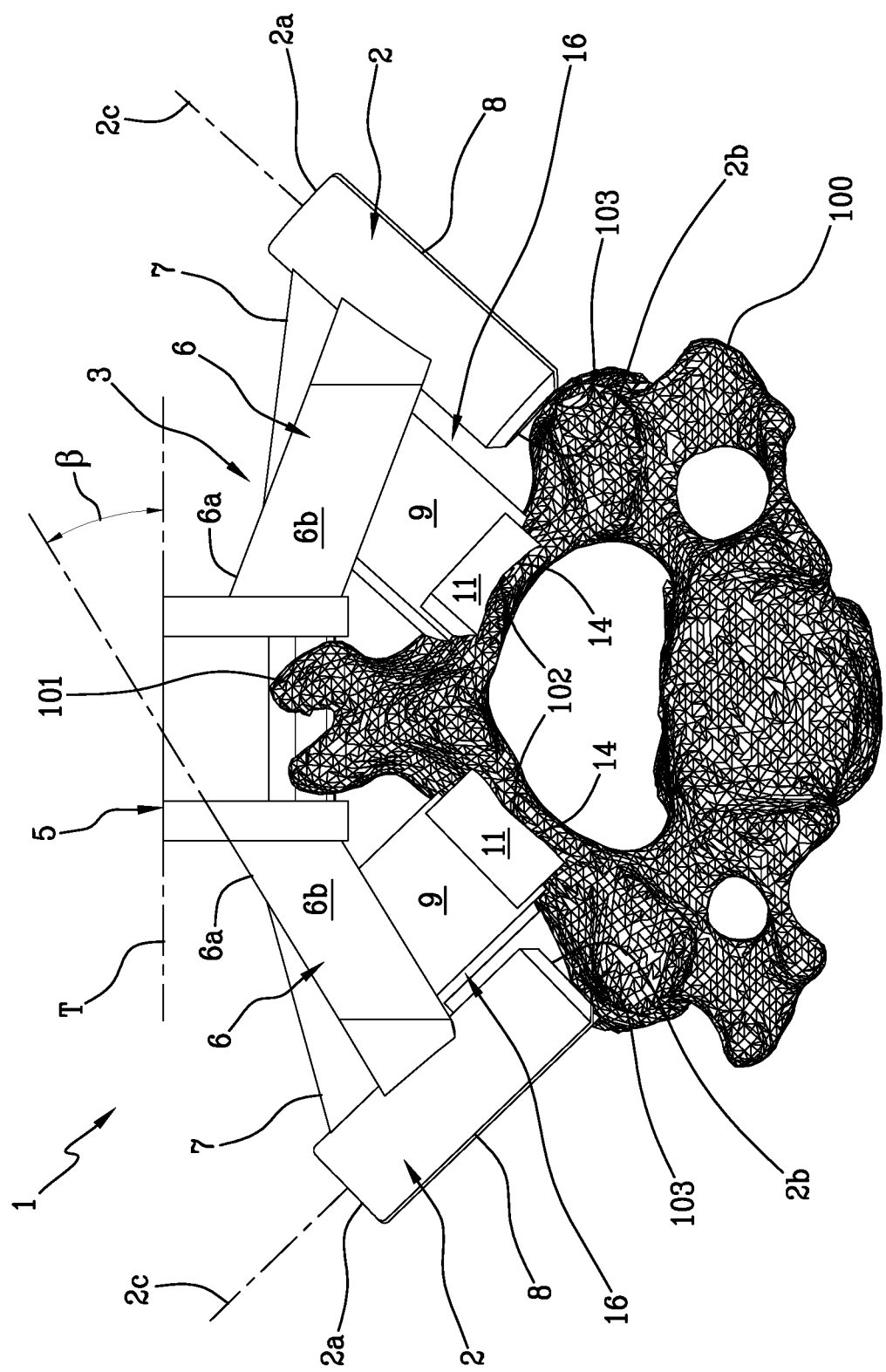
FIG. 4 is a front view of the guide in accordance with the present invention.

The supporting frame 3 comprises two arms 6, each connected to a tubular guiding member 2 and converging into a bridge 5, which can be positioned above the spinous process 101 of the vertebra 100, with or without any contact therewith. Said bridge 5 may be in a so-called closed configuration (as shown in FIGS. 1, 2, 3), i.e. generating a cage for receiving the spinous process 101, or in an open configuration, i.e. creating an open housing (configuration not illustrated), alternately in a semi-open configuration, as shown in FIG. 4, i.e. generating a partial cage for receiving the spinous process 101.

Figure 5:
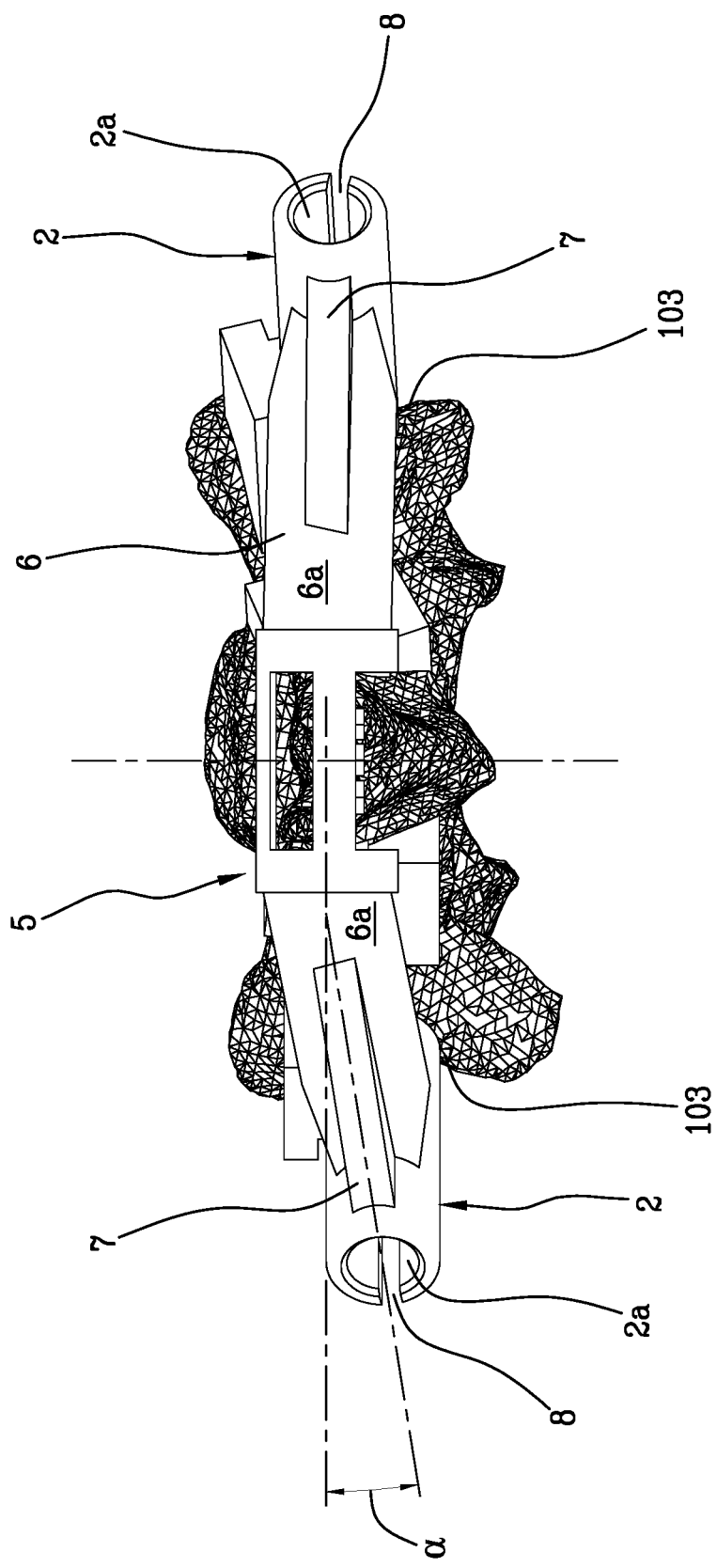
FIG. 5 is a top plan view of the guide in accordance with the present invention.

Referring to FIG. 5, each arm 6, defining a transverse median vertical plane passing through the bridge 5, is contained in a respective vertical plane, passing through the longitudinal axis 2c of each tubular guide 2, inclined by an angle α comprised between −30° and +60° with respect to the through median vertical plane of the bridge 5, where the negative value of the angle α is understood as the inclination in the caudal direction. As can be seen in FIG. 4, a proximal surface 6a of each arm 6 forms, with a plane T tangent to the top of the bridge 5, an angle β comprised between 0° and 50°, preferably between 5° and 50°.

This arrangement allows the stability of the guide 1 to be improved.

The navigational guide object of the present invention is preferably intended for use with cervical vertebrae, which therefore exhibit considerably reduced dimensions.

As the available space is reduced, it was essential to think about how to ensure the stability and structural stiffness of the guide while reducing the occupied volume.

The known guides have the risk of deforming, which causes a deviation between the planned and the actual position of the screw. The screw may be positioned incorrectly and seriously damage the patient's neural and/or bone structure during these kinds of applications. A non-straight bridge, in addition to that generated by the two arms and the bridge 5, is known to improve the stability of the guide, as regards the medial lateral deformation at the position of the K-wire/screw entry point.

The arrangement of the non-straight bridge prevents any deflection of the guide (i.e., the two tubular guiding members 2 cannot approach one another) and ensures the accuracy of the K-wire/screw positioning. By contrast, however, the non-straight bridge needs a further volume and provides greater dimensions that, in case of application to cervical vertebrae, are not available.

In order to overcome this problem, the two arms were devised to be arranged in an almost coplanar configuration, in which the two arms deviate from the coplanarity by an angle α comprised, as said, between −30° and +60°.

Each of the two arms 6 has a prismatic shape defined by planar surfaces 6a-6d. The prismatic shape of the arms 6 widens from the tubular guiding member 2 to the bridge 5. In particular, each arm 6 comprises a proximal surface 6a and a distal surface 6c, opposite to the proximal surface 6a, each having a substantially triangular shape, and two opposite side planar surfaces 6b, 6d, each having a substantially rectangular shape.

Each arm 6 is connected to the two tubular guiding members 2 at a substantially central portion of each tubular guiding member 2, between the proximal opening 2a and the distal opening 2b.

In particular, the width L of the two opposite planar surfaces 6b and 6d of each arm 6 defines a connecting portion extending between the tubular guiding members 2 and the bridge 5. Preferably, the width L is larger than A/2, wherein A is the distance between the proximal opening 2a and the distal opening 2b.

Reinforcing ribs 7 can be provided to connect the arms 6 to the tubular guiding members 2. In particular, each rib 7 extends from a portion near the proximal opening 2a to the proximal surface 6a of each arm 6.

The frame 3 is contained within an inner volume defined by the two tubular guiding members 2.

Each tubular guiding member 2 has a slot 8 extending from the proximal opening 2a to the distal opening 2b.

Each slot 8 extends parallel to the axial direction of the respective tubular guide 2 and is directed outwardly with respect to a volume defined by the two tubular guides 2.

These slots 8 facilitate the removal of the navigational guide at the end of the steps for insertion of the K-wires, preventing any possible displacement of the same once positioned. In this way, once said K-wires have been positioned, the surgeon can proceed with the removal of the navigational guide by simply lifting it from its position in contact with the vertebra.

Stability is further guaranteed by the high number of contact points in the guide, as will be explained hereinbelow.

The pre-operative planning is performed, by means of computer-aided design tools, on a three-dimensional model of the bone structure developed from a three-dimensional image (e.g., computed tomography image/magnetic resonance) of the patient. Therefore, the navigational guide 1 is designed so that it uniquely matches the bone structure of the patient.

In particular, to ensure a correct and stable positioning of the navigational guide 1, a plurality of contact members is provided, each of them being designed to match a corresponding contact area on the patient's vertebra 100.

Advantageously, the main contact areas correspond to the laminae 102 and the superior articular process 103 or facet.

The plurality of contact members comprises a pair of a first main contact member 15 adapted to mate with a contact area corresponding to the superior articular process 103 or facet of the vertebra 100.

In the present embodiment, each of the first main contact members 15 comprises a contact tooth, projecting from the respective tubular guiding member 2, near the distal opening 2b, below the bridge 5. The free end of these contact teeth is designed with a shape matching the superior articular process 103 or facet of the patient's vertebra 100. It should be noted that the contact tooth extends from a caudal/inner portion of the tubular guiding member 2 and is directed toward the median plane and away from the vertex of the bridge 5.

In a further embodiment, not illustrated, the contact tooth is not present and the distal opening 2b is shaped so as to mate with the anatomical shape of the superior articular process or facet, thereby defining the main contact member.

The plurality of contact members also comprises a pair of a second main contact member 16, designed to abut on a contact area corresponding to the laminae 102 of the patient's vertebra 100.

Each second main contact member 16 extends from a respective arm 6, abutting on the lamina 102 of the vertebra 100. Preferably, each second main contact member 16 comprises a lamella 9, having a planar, preferably polygonal shape, which extends in a direction substantially parallel to the longitudinal axes 2c of the tubular guiding members 2. Preferably, these lamellae 9 have a transverse extension comprised between 5 and 60 mm, preferably between 5 and 40 mm.

Each second main contact member 16 further comprises a pair of pins 11 designed to abut on a contact area corresponding to the laminae 102 of the patient's vertebra 100, so as to ensure greater stability in the sagittal direction.

As can be seen in the appended figures, each pin 11 protrudes transversely and in opposite directions from each lamella 9.

Advantageously, each pair of pins 11 defines a single bearing surface with the free base, opposite to the arms 6, of the corresponding lamella 9 from which they project.

Preferably, each pin 11 has a respective lip 14 adapted to envelop the lamina 102 and avoid any translations and misalignments of the navigational guide with respect to the vertebra 100.

The presence of the pins 11 and related lips 14 allows a combined and strengthened support since the resulting contact surface is greater: in addition to the support given by the lamella 16 of the second main contact members, which rests on the lamina 102, there is also the contact of the pins, while the lip 14 of each pin better envelops a portion of the vertebra 100, almost "clinging" to it.

Preferably, each pin 11 has minimum dimensions in width (i.e. along the direction extending from one tubular guiding member to another) and height (the direction extending from the proximal opening to the distal opening) of at least 3 mm; preferably it protrudes from the lamella by at least 1 mm.

The first two main contact members 15, as well as the second two main contact members 16, are symmetrically positioned on the navigational guide 1, with respect to a median plane passing through the bridge 5. However, depending on the patient's anatomy, an asymmetrical arrangement is also possible.

Again with respect to a median plane passing through the bridge 5, the first two main contact members 15 are placed laterally and externally with respect to the second two main contact members 16; in other words, the second main contact members 16 are positioned between the bridge 5 and the first main contact members 15.

The surgical procedure employing a patient-specific navigational guide 1 comprises a pre-operative planning and an intra-operative procedure.

The pre-operative planning comprises a first step of acquiring computed tomography images/magnetic resonance of the surgical site, a second step of reconstructing a three-dimensional image of the site, and a third step of planning the positioning of a generic surgical instrument (screws, K-wire or burr) on the three-dimensional image by means of computer-aided design tools.

Once the axes of the screw or the cutting planes have been identified, the steps of designing and manufacturing the patient-specific navigational guide 1 are performed.

The intra-operative procedure is described below with reference to the patient-specific guide 1.

The procedure comprises a step of cleaning the vertebrae without however cutting the ligaments, since the guide does not contact the upper part of the spinous process. The intra- and/or supra-spinous ligaments are preserved, so as to allow a faster and easier insertion of the guide. The surgery is thus less invasive for the patient and the surgeon will have fewer steps to perform (less soft tissue to be removed) with consequent reduction of the margin of error.

Subsequently, a step is provided to couple the guide to the clean vertebra. It should be noted that, prior to the coupling, the correct location and alignment of the guiding members 2 can be checked on a real size three-dimensional model of the vertebra.

After the coupling, two awls are inserted in the tubular guiding members 2. After removal of the awls, the surgeon can check the entry points for the pedicle screws. In the next step, the pedicle of the vertebra is opened with a probe or drill inserted in the guiding member 2. The surgeon may use a feeler for help in the process. Finally, after removing the probes or drills, the pedicle screws can be inserted through the tubular guiding members 2 by means of a screwdriver.

In an alternative method, the adapter sleeve is capped on top of the tubular guiding members 2 and two Kirchner wires are inserted in the vertebra instead of directly fixing the pedicle screws. After removal of the navigational guide, the Kirchner wires are used to guide the insertion of a cannulated pedicle screw.

The presence of the lateral slots 8 along the tubular guides 2 allows a quick and safe removal of the navigational guide without undermining the stability and the correct position of the K-wires.

Obviously a person skilled in the art, in order to meet specific needs, will readily acknowledge that changes and variations to the navigational guides described above are possible within the scope of protection as defined by the following claims.

The invention claimed is:

1. A patient-specific navigational guide for use in spinal surgery, comprising:
    two monolithic tubular guiding members integral with a supporting frame, each tubular guiding member defining a channel having a proximal opening and a distal opening for guiding a surgical operation on a patient's vertebra; and
    contact members designed to mate with a corresponding plurality of contact areas on the patient's vertebra in order to define a unique coupling configuration of the patient-specific navigational guide on the patient's vertebra, wherein said contact members comprise at least one pair of first main contact members, designed to abut, at least partially, on the upper articular process, or facet, of the patient's vertebra, and a pair of second main contact members, designed to abut on a contact area corresponding to the lamina of the patient's vertebra,
    wherein each tubular guiding member defines a longitudinal slot that extends continuously from the proximal opening to the distal opening and is in communication with the channel.

2. The patient-specific navigational guide according to claim 1, wherein each longitudinal slot extends parallel to the axial direction of the respective tubular guiding member and is directed outwardly with respect to a volume defined by the two tubular guiding members.

3. The patient-specific navigational guide according to claim 1, wherein the supporting frame comprises two arms, each arm being connected to a respective one of the tubular guiding members, converging into a bridge designed to be arranged above the spinous process of the patient's vertebra.

4. The patient-specific navigational guide according to claim 3, wherein each of the first main contact members comprises a contact tooth, projecting from a respective one of the tubular guiding members near the distal opening.

5. The patient-specific navigational guide according to claim 3, wherein a respective one of the second main contact members extends from each arm.

6. The patient-specific navigational guide according to claim 1, wherein each second main contact member comprises a respective lamella extending in a direction substantially parallel to the longitudinal axes of the tubular guiding members.

7. The patient-specific navigational guide according to claim 6, wherein each second main contact member comprises a pair of pins, designed to abut on a contact area corresponding to the laminae of the patient's vertebra.

8. The patient-specific navigational guide according to claim 7, wherein said pins protrude transversely and in opposite directions from each lamella.

9. The patient-specific navigational guide according to claim 8, wherein said pins define a single bearing surface with the free base of said lamella, opposite to the arms.

10. The patient-specific navigational guide according to claim 9, wherein each pin has a respective lip adapted to envelop the lamina.

11. The patient-specific navigational guide according to claim 1, wherein said arms lie in respective vertical planes containing the longitudinal axes of the tubular guides, defining an angle of between −30° and +60° therebetween.

12. The patient-specific navigational guide according to claim 1, wherein each arm has a proximal surface inclined relative to a plane tangent to the top of the bridge by an angle comprised between 0° and 60°.

13. The patient-specific navigational guide according to claim 12, wherein the angle is between 5° and 50°.

* * * * *